United States Patent
Brianti et al.

(10) Patent No.: US 9,422,205 B2
(45) Date of Patent: Aug. 23, 2016

(54) PROCESS FOR THE PRODUCTION OF HIGH-PURITY ISOBUTENE THROUGH THE CRACKING OF MTBE OR ETBE AND INTEGRATED PROCESS FOR THE PRODUCTION OF THE RELATIVE ETHER

(71) Applicant: Saipem S.P.A., San Donato Milanese (MI) (IT)

(72) Inventors: Maura Brianti, Busto Arsizio (IT); Massimo Conte, Peschiera Borromeo (IT)

(73) Assignee: Saipem S.P.A., San Donato Milanese, Milan (IT)

( * ) Notice: Subject to any disclaimer, the term of this patent is extended or adjusted under 35 U.S.C. 154(b) by 0 days.

(21) Appl. No.: 14/433,098

(22) PCT Filed: Oct. 4, 2013

(86) PCT No.: PCT/EP2013/070731
§ 371 (c)(1),
(2) Date: Apr. 2, 2015

(87) PCT Pub. No.: WO2014/053645
PCT Pub. Date: Apr. 10, 2014

(65) Prior Publication Data
US 2015/0251968 A1    Sep. 10, 2015

(30) Foreign Application Priority Data

Oct. 5, 2012  (IT) .............................. MI2012A1673

(51) Int. Cl.
*C07C 1/20* (2006.01)
*C07C 41/06* (2006.01)
*C07C 29/10* (2006.01)

(52) U.S. Cl.
CPC ................. *C07C 1/20* (2013.01); *C07C 29/10* (2013.01); *C07C 41/06* (2013.01)

(58) Field of Classification Search
None
See application file for complete search history.

(56) References Cited

U.S. PATENT DOCUMENTS 6,072,095 A * 6/2000 Marion ..................... C07C 1/20 585/639
6,143,936 A * 11/2000 Marion ..................... C07C 11/02 568/579
6,696,612 B2 * 2/2004 Yamase ..................... C07C 1/20 568/909
6,852,899 B2 * 2/2005 Yamase ..................... C07C 1/20 585/639

OTHER PUBLICATIONS

Database CAPLUS in STN, Acc. No. 2013:1008579, Yao et al., CN 103172487 A (Jun. 26, 2013) (abstract).*
Database CAPLUS in STN, Acc. No. 2008:1110646, Liu et al., CN 101260016 A (Sep. 10, 2008) (abstract).*
Database CAPLUS in STN, Acc. No. 2007:967285, Yang et al., CN 101024595 A (Aug. 29, 2007) (abstract).*
Database CAPLUS in STN, Acc. No. 2003:746945, Zhou et al., CN 1358699 A (Jul. 17, 2002) (abstract).*
Database CAPLUS in STN, Acc. No. 2003:746944, Zhou et al., CN 1358698 A (Jul. 17, 2002) (abstract).*
Database CAPLUS in STN, Acc. No. 2002:837809, Zhou et al., Shiyou Huagong (2002), 31(8), pp. 638-640 (abstract).*

* cited by examiner

*Primary Examiner* — Brian J Davis
(74) *Attorney, Agent, or Firm* — MacMillan, Sobanski & Todd, LLC (57) ABSTRACT

Process for the production of high-purity isobutene starting from a stream prevalently containing MTBE (Methyl-Tert Butyl Ether) or ETBE (Ethyl-Tert Butyl Ether) which essentially comprises the following areas in sequence: • a fractionation area for obtaining a stream of high-purity MTBE or ETBE; • a cracking area of said stream of MTBE or ETBE for obtaining an outgoing stream prevalently containing isobutene and the relative alcohol, methanol or ethanol; • a washing area with water of the stream leaving the cracking area for the recovery of the relative alcohol, in order to obtain a stream containing isobutene, the ether fed and light compounds and a stream substantially consisting of water and relative alcohol, with a relevant fractionation section for separating the washing water to be recycled to the same washing area from the relative alcohol; • a fractionation area of the stream containing isobutene, the ether fed and light compounds for separating a stream of high-purity isobutene. The process can be possibly integrated with a process for the production of MTBE or ETBE.

21 Claims, 4 Drawing Sheets

PROCESS FOR THE PRODUCTION OF HIGH-PURITY ISOBUTENE THROUGH THE CRACKING OF MTBE OR ETBE AND INTEGRATED PROCESS FOR THE PRODUCTION OF THE RELATIVE ETHER

This is a national stage application filed under 35 U.S.C. §371 of international application PCT/EP2013/070731, filed under the authority of the Patent Cooperation Treaty on Oct. 4, 2013, published; which claims the benefit of Italian Patent Application No. MI2012A001673, filed on Oct. 5, 2012. The entire disclosures of all the aforementioned applications are expressly incorporated herein by reference for all purposes.

The present patent application relates to a process for the production of high-purity isobutene through the cracking of MTBE (methyl-tert butyl ether) or ETBE (ethyl-tert butyl ether) and an integrated process for the production of the relative ether (MTBE or ETBE).

The process for the production of isobutene is an endothermic cracking reaction typically of commercial MTBE, i.e. with a purity degree normally higher than 98% by weight (according to the sales specification).

The reaction takes place in the presence of an extremely selective catalyst without any problems of corrosion, which should have a relatively long life cycle, without creating problems of toxicity for the environment.

The catalyst must be acid and active: the activity guarantees a high conversion of MTBE per reaction step, whereas the acidity limits side-reactions and the formation of byproducts.

The cracking reaction takes place in vapour phase in a tubular reactor in which the catalyst is positioned at the tube side, with a conversion of MTBE higher than 80%, operating at a temperature ranging from 100 to 300° C., using vapour at a suitable pressure or diathermic oil, as heating means.

The production plant of isobutene from the cracking of oxygenated compounds is generally divided into three sections: a reaction section, a section for the recovery and purification of isobutene and a section for the recovery of methanol and its possible purification.

The isobutene is then used in plants for the production of rubber or for the production of chemicals.

The production scheme generally consists of reactor, fractionation and washing column in sequence.

From the production schemes of isobutene of the known art, it is difficult to effect:
  the separation of the azeotropic mixtures (MTBE-methanol; MTBE-TBA; etc.) among the products formed during the reaction and the subsequent separation and washing phase;
  the production of methanol with a high purity degree (there are in fact two production schemes of methanol, one with a purity of 95% suitable for producing MTBE and the other, commercially defined as Grade A, suitable for being sold, with a purity of 99.85%);
  the control of the generation of side-reactions and hence the formation of byproducts.

It has now been found that the disadvantages of the known art indicated above can be eliminated or substantially reduced by means of a solution which comprises inverting the washing column with the fractionation column, consequently positioning the washing column before the fractionation column, thus avoiding having to operate in the presence of azeotropic mixtures which are difficult to separate.

All the methanol (or ethanol in the case of ETBE) and water are recovered during the washing thus facilitating the recovery of unconverted MTBE (or ETBE).

In particular, in the case of MTBE, in order to control the formation of by-products, above all DME, a side-stream present in the case of methanol Grade A or the water recovered from the condensates produced in the plant, is recycled to the reactor.

The process, object of the present invention, for the production of high-purity isobutene starting from a stream prevalently containing MTBE (Methyl-Tert Butyl Ether) or ETBE (Ethyl-Tert Butyl Ether) essentially comprises the following areas in sequence:
  a fractionation area for obtaining a stream of high-purity MTBE or ETBE;
  a cracking area of said stream of MTBE or ETBE for obtaining an outgoing stream prevalently containing isobutene and the relative alcohol, methanol or ethanol;
  a washing area with water of the stream leaving the cracking area for the recovery of the relative alcohol, in order to obtain a stream containing isobutene, the ether fed and light compounds and a stream substantially consisting of water and relative alcohol, with a relevant fractionation section for separating the washing water to be recycled to the same washing area from the relative alcohol;
  a fractionation area of the stream containing isobutene, the ether fed and light compounds for separating a stream of high-purity isobutene. In particular, when starting from a stream prevalently containing MTBE, the process essentially comprises the following areas in sequence:
  a fractionation area for obtaining a stream of MTBE having a purity higher than 98% by weight;
  a cracking area of said stream of MTBE for obtaining an outgoing stream prevalently containing methanol and isobutene;
  a washing area with water of the stream leaving the cracking area for the recovery of the methanol to obtain a stream containing isobutene, MTBE and light compounds and a stream substantially consisting of water and methanol, with a relevant fractionation section for separating the washing water to be recycled to the same washing area from the methanol;
  a fractionation area of the stream containing isobutene, MTBE and light compounds for separating a stream of high-purity isobutene.

Said process for the production of isobutene starting from MTBE preferably comprises the following steps:
  feeding a stream containing MTBE to one or more fractionation columns for the purification of the MTBE, separating a stream containing MTBE and compounds lighter than MTBE, a stream of MTBE having a purity higher than 98% by weight and a stream containing MTBE and compounds heavier than MTBE;
  feeding the stream of MTBE having a purity higher than 98% by weight to one or more cracking reactors obtaining an outgoing stream consisting of cracking products and non-converted reagents;
  feeding the outgoing stream consisting of cracking products and non-converted reagents to a washing column with water, separating a stream containing isobutene, MTBE and light compounds at the head, and a stream prevalently containing methanol and water at the bottom, in turn sent to one or more fractionation columns for separating the water, to be recycled to the washing column, from the methanol;

feeding the stream separated from the head of the washing column to a fractionation column for separating the isobutene from the MTBE, obtaining a stream containing isobutene and light compounds at the head, and a stream containing MTBE and heavier compounds at the bottom;

feeding the stream separated from the head of the fractionation column containing isobutene and light compounds to another fractionation column for the purification of the isobutene, obtaining a stream containing light compounds at the head and a stream of high-purity isobutene at the bottom.

The stream at the bottom of the washing column containing methanol and water can be sent to a single fractionation column, separating a stream containing methanol and ethers at the head, and at the bottom, water recycled to the washing column or to a first fractionation column, separating high-octane mixtures (HOM) at the head, substantially consisting of alcohols and ethers, and a stream of water and methanol at the bottom, which is sent to a second fractionation column, separating a stream of high-purity methanol, Grade A, at the head, and the water recycled to the washing column at the bottom.

A stream, recycled to the cracking reactor(s), can also be removed laterally from the possible second fractionation column of the stream of water and methanol.

The stream at the bottom containing MTBE of the fractionation column for separating isobutene from MTBE may preferably be recycled to the fractionation column(s) for purifying MTBE.

The fractionation column for the purification of MTBE can operate at a pressure ranging from 1 to 12 $bar_g$, preferably from 4 to 8 $bar_g$.

The cracking reactor(s) can operate at a temperature ranging from 100 to 300° C., preferably from 150 to 240° C., and at a pressure ranging from 1 to 10 $bar_g$, preferably from 3 to 6 $bar_g$.

The cracking reactor(s) can operate with a wide variety of acid catalysts selected from ion exchange resins, suitably modified zeolites, catalysts based on silicified alumina, boralites, zeolites and silica suitably modified. Among these catalysts, the use of silica modified with the addition of alumina in a quantity ranging from 0.1 to 3% by weight (EP-524679) is preferred.

The washing column of the stream leaving the cracking reactor(s) can operate at a temperature ranging from 20 to 100° C., preferably from 30 to 50° C., and at a pressure ranging from 2 to 15 $bar_g$, preferably from 6 to 9 $bar_g$.

The fractionation column for the separation of isobutene from the MTBE can operate at a pressure at the head ranging from 2 to 10 $bar_g$, preferably from 4 to 6 $bar_g$.

The fractionation column for the purification of isobutene can operate at a pressure at the head ranging from 2 to 15 $bar_g$, preferably from 6 to 9 $bar_g$.

The fractionation column(s) of the stream prevalently containing methanol and water coming from the bottom of the washing column can operate at a pressure at the head ranging from atmospheric pressure to 10 $bar_g$, preferably from 0.1 to 5 $bar_g$.

A further object of the present invention relates to the integrated process for the production of MTBE or ETBE and high-purity isobutene.

The integrated process for the production of MTBE or ETBE and high-purity isobutene, starting from streams prevalently containing $C_4$ hydrocarbons, essentially comprises the following areas, already described above for the production of isobutene:

a fractionation area for obtaining a stream of high-purity MTBE or ETBE;

a cracking area of said stream of MTBE or ETBE for obtaining an outgoing stream prevalently containing isobutene and the relative alcohol, methanol or ethanol;

a washing area with water of the stream leaving the cracking area for the recovery of the relative alcohol to obtain a stream containing isobutene, the ether fed and light compounds and a stream substantially consisting of water and the relative alcohol, with a relevant fractionation section for separating the washing water to be recycled to the same washing area from the relative alcohol;

a fractionation area of the stream containing isobutene, the ether fed and light compounds for separating a stream of high-purity isobutene;

integrated by the following areas:

an etherification area fed by streams prevalently containing $C_4$ hydrocarbons and the relative alcohol to obtain the stream containing the ether obtained, $C_4$ hydrocarbons and the relative alcohol to be fed to the same fractionation area for obtaining the stream of high-purity MTBE or ETBE;

a possible additional etherification area with a relevant fractionation section, for separating a stream containing $C_4$ hydrocarbons and the relative alcohol and a stream containing the ether obtained, $C_4$ hydrocarbons and the relative alcohol to be fed to the first fractionation area;

a washing area with water of said stream containing $C_4$ hydrocarbons and the relative alcohol, coming from the fractionation area, to obtain the stream of high-purity ether, MTBE or ETBE, or from the fractionation section of the possible additional etherification area, with a relevant fractionation section, for separating the washing water to be recycled to the washing area itself, said relevant fractionation section for separating the washing water being the same relevant fractionation section of the washing area of the stream leaving the cracking area for separating the stream containing isobutene.

In particular, the integrated process for the production of MTBE and high-purity isobutene, starting from streams prevalently containing $C_4$ hydrocarbons, essentially comprises the following areas, already described above for the production of isobutene:

a fractionation area for obtaining a stream of MTBE having a purity higher than 98% by weight;

a cracking area of said stream of MTBE for obtaining an outgoing stream prevalently containing methanol and isobutene;

a washing area with water of the stream leaving the cracking area for the recovery of the methanol to obtain a stream containing isobutene, MTBE and light compounds and a stream substantially consisting of water and methanol, with a relevant fractionation section for separating the washing water to be recycled to the washing area from the methanol;

a fractionation area of the stream containing isobutene, MTBE and light compounds for separating a stream of high-purity isobutene;

integrated by the following areas:

an etherification area fed by streams prevalently containing $C_4$ hydrocarbons and methanol to obtain a stream containing MTBE, $C_4$ hydrocarbons and methanol to be fed to the same fractionation area for obtaining the stream of MTBE having a purity higher than 98% by weight;

a possible additional etherification area with a relevant fractionation section, for separating a stream containing $C_4$ hydrocarbons and methanol and a stream containing MTBE, $C_4$ hydrocarbons and methanol to be fed to the first fractionation section;

a washing area with water of said stream containing $C_4$ hydrocarbons and methanol, coming from the fractionation area, to obtain the stream of MTBE having a purity higher than 98% by weight, or from the possible fractionation section of the possible additional etherification area, with a relevant fractionation section, for separating the washing water to be recycled to the washing area itself, said relevant fractionation section for separating the washing water being the same relevant fractionation section of the washing water of the stream leaving the cracking area for separating the stream containing isobutene.

Said integrated process for the production of MTBE preferably essentially comprises the following steps already described above for the production of isobutene:

feeding a stream containing MTBE to one or more fractionation columns for the purification of the MTBE, separating a stream containing MTBE and compounds lighter than MTBE, a stream of MTBE having a purity higher than 98% by weight and a stream containing MTBE and compounds heavier than MTBE;

feeding the stream of MTBE having a purity higher than 98% by weight to one or more cracking reactors obtaining an outgoing stream consisting of cracking products and non-converted reagents;

feeding said outgoing stream consisting of cracking products and non-converted reagents to a washing column with water, separating a stream containing isobutene, MTBE and light compounds at the head, and a stream containing methanol and water at the bottom, in turn sent to one or more fractionation columns for separating the water, to be recycled to the washing column, from the methanol;

feeding the stream separated from the head of the washing column to a fractionation column for separating the isobutene from the MTBE, obtaining a stream containing isobutene and light compounds at the head, and a stream containing MTBE and heavier compounds at the bottom;

feeding the stream separated from the head of the fractionation column containing isobutene and light compounds to another fractionation column for the purification of the isobutene, obtaining a stream containing light compounds at the head and a stream of high-purity isobutene at the bottom, integrated, in the case of a single etherification area, by the following steps:

feeding the stream prevalently containing $C_4$ hydrocarbons and methanol to one or more etherification reactors obtaining a stream containing MTBE, $C_4$ hydrocarbons and methanol to be fed to the same fractionation column(s) for the purification of the MTBE;

feeding the stream containing MTBE and compounds lighter than MTBE, among which $C_4$ hydrocarbons, separated in the same fractionation column(s) for the purification of MBTE, to an additional washing column with water, separating a stream of $C_4$ hydrocarbons at the head, and a stream containing methanol and water at the bottom, in turn sent to one or more fractionation columns for separating the water, to be recycled to the washing column, from the methanol, the fractionation column(s) for separating the water from the methanol being the same fractionation column(s) to which the stream at the bottom of the washing column of the stream leaving the cracking reactor, is sent, or integrated, in the case of two etherification areas, by the following steps:

feeding the stream prevalently containing $C_4$ hydrocarbons and methanol to one or more etherification reactors obtaining a stream containing MTBE, $C_4$ hydrocarbons and methanol to be fed to the same fractionation column(s) for the purification of MTBE;

feeding the stream containing MTBE and compounds lighter than MTBE, among which $C_4$ hydrocarbons, separated in the same fractionation column(s) for the purification of MBTE, to another etherification reactor(s) obtaining a further stream containing MTBE, $C_4$ hydrocarbons and methanol;

feeding the further stream containing MTBE, $C_4$ hydrocarbons and methanol to another fractional column obtaining a stream containing $C_4$ hydrocarbons and methanol at the head and a stream containing MTBE at the bottom, which is recycled to the fractionation column for the purification of the MTBE;

feeding the stream at the head containing $C_4$ hydrocarbons and methanol to a further washing column with water, separating a stream of $C_4$ hydrocarbons at the head, and a stream containing methanol and water at the bottom, in turn sent to one or more fractionation columns for separating the water, to be recycled to the washing column, from the methanol.

the fractionation column(s) for separating the water from the methanol being the same fractionation column(s) to which the stream at the bottom of the washing column of the stream leaving the cracking reactor, is sent.

The purification step of MTBE, both in the case of one etherification area and in the case of two etherification areas, is preferably effected in a single fractionation column.

The etherification reactor(s) can operate with a wide variety of acid catalysts selected from mineral acids (e.g. sulfuric acid, $BF_3$, supported phosphoric acid), zeolites suitably modified, heteropolyacids and sulfonated polymeric resins, for example Amberlyst 15, Amberlyst 35, Amberlyst 36, etc. Among these catalysts, the use of macroreticular sulfonated resins, generally copolymers of styrene and divinylbenzene, is preferred. The characteristics of these resins are widely described in literature (see for example A. Mitschker, R. Wagner, P. M. Lange, "Heterogeneous Catalysis and fine Chemicals", M. Guisnet ed, Elsevier, Amsterdam (1988)).

The reaction can be carried out in tubular or adiabatic reactors, either in vapour phase or liquid phase, liquid phase being preferred.

The preferred operating conditions for operating in liquid phase are: a temperature ranging from 20 to 150° C., preferably from 30 to 100° C., and a pressure lower than 50 $bar_g$, preferably from 2 to 25 $bar_g$.

The additional washing column of the stream containing $C_4$ hydrocarbons and methanol can operate at a temperature ranging from 20 to 100° C., preferably from 30 to 50° C. and at a pressure ranging from 2 to 30 $bar_g$ preferably from 10 to 15 $bar_g$.

The disclosures provided in the description for MTBE can also be easily applied to ETBE, for an expert in the field.

Some preferred embodiments of the invention are now provided with the help of the enclosed FIGS. 1-4 which should not be considered as limiting the scope of the invention itself.

Figure 1:
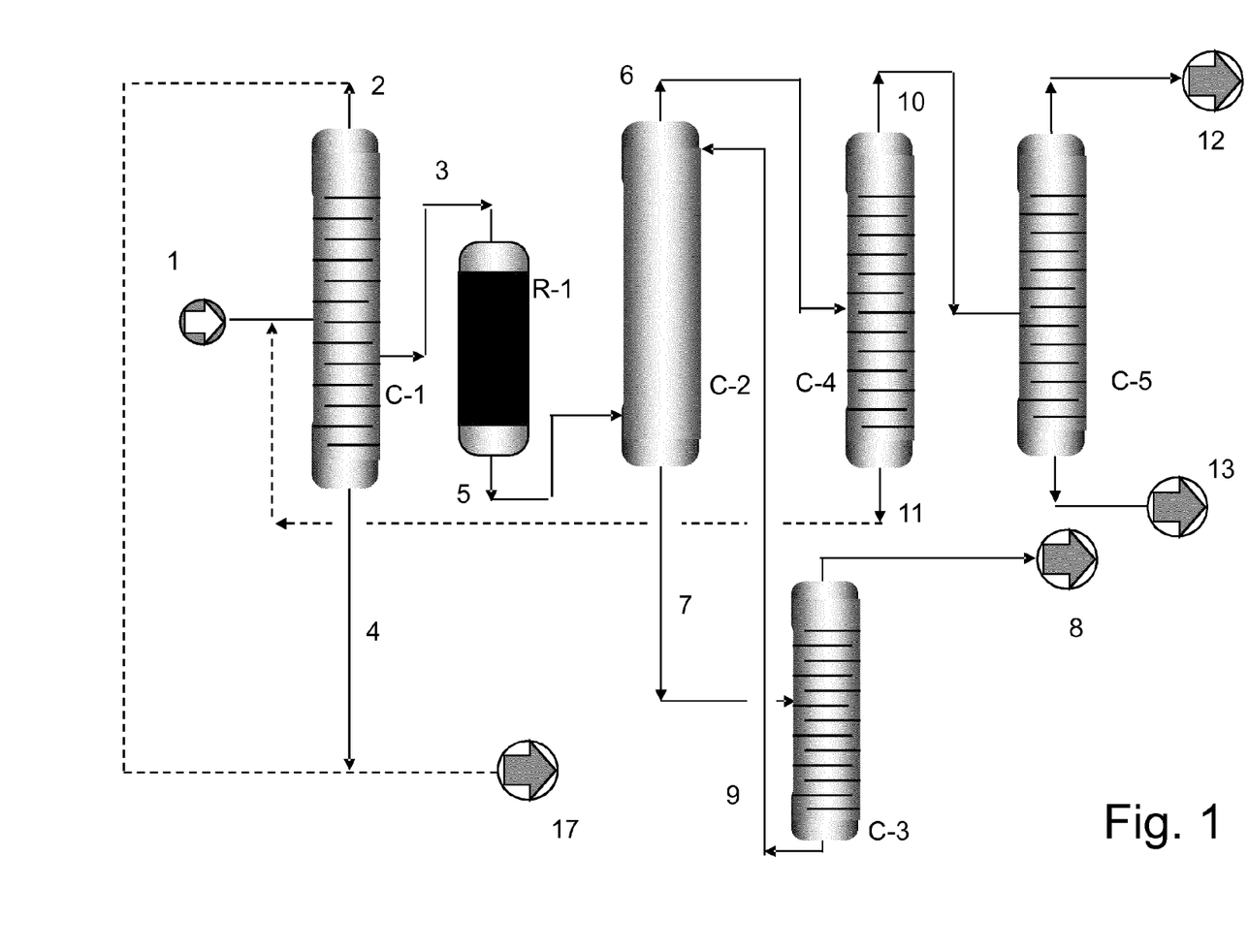
FIG. 1: Scheme for the production of high-purity isobutene.

FIG. 1 shows a scheme for the production of high-purity isobutene.

A stream (1) prevalently containing MTBE is fed to a fractionation column (C-1) for the purification of the MTBE, from which a stream (2) containing MTBE and compounds lighter than MTBE is separated at the head, a stream (3) of MTBE having a purity higher than 98% by weight is separated laterally and a stream (4) containing MTBE and compounds heavier than MTBE is separated at the bottom.

The stream (3) of MTBE having a purity higher than 98% by weight is sent to a cracking reactor (R-1) from which a stream (5) containing the cracking products and non-reacted reagents exits, which is fed to a washing column (C-2) with water, from which a stream (6) containing isobutene, MTBE and light compounds is separated at the head and a stream (7) prevalently containing methanol and water at the bottom, which is sent to a fractionation column (C-3) for the separation of the methanol from the water, obtaining a stream (8) at the head, containing methanol, and a stream (9) at the bottom, containing water, which is sent to the washing column (C-2).

The stream (6) containing isobutene, MTBE and light compounds is sent to a fractionation column (C-4) for the separation of the isobutene from the MTBE, obtaining, at the head, a stream (10) containing isobutene and light compounds, which, in turn, is sent to a fractionation column (C-5) for purification of the isobutene, and at the bottom, a stream (11) containing non-converted MTBE.

From the fractionation column (C-5), a stream (12) containing light compounds is separated at the head, and a stream (13) of high-purity isobutene, at the bottom.

Stream (11) containing MTBE can be possibly recycled to the fractionation column (C-1).

Streams (2) and (4), containing MTBE and respectively compounds lighter than MTBE and compounds heavier than MTBE, among which di-isobutene, can be possibly joined (called HOM (High octane mixture)) and sent to a gasoline pool. The stream (8) containing methanol leaving the fractionation column (C-3) has a percentage of MTBE which is such as to allow it to be used for the production of MTBE.

Figure 2:
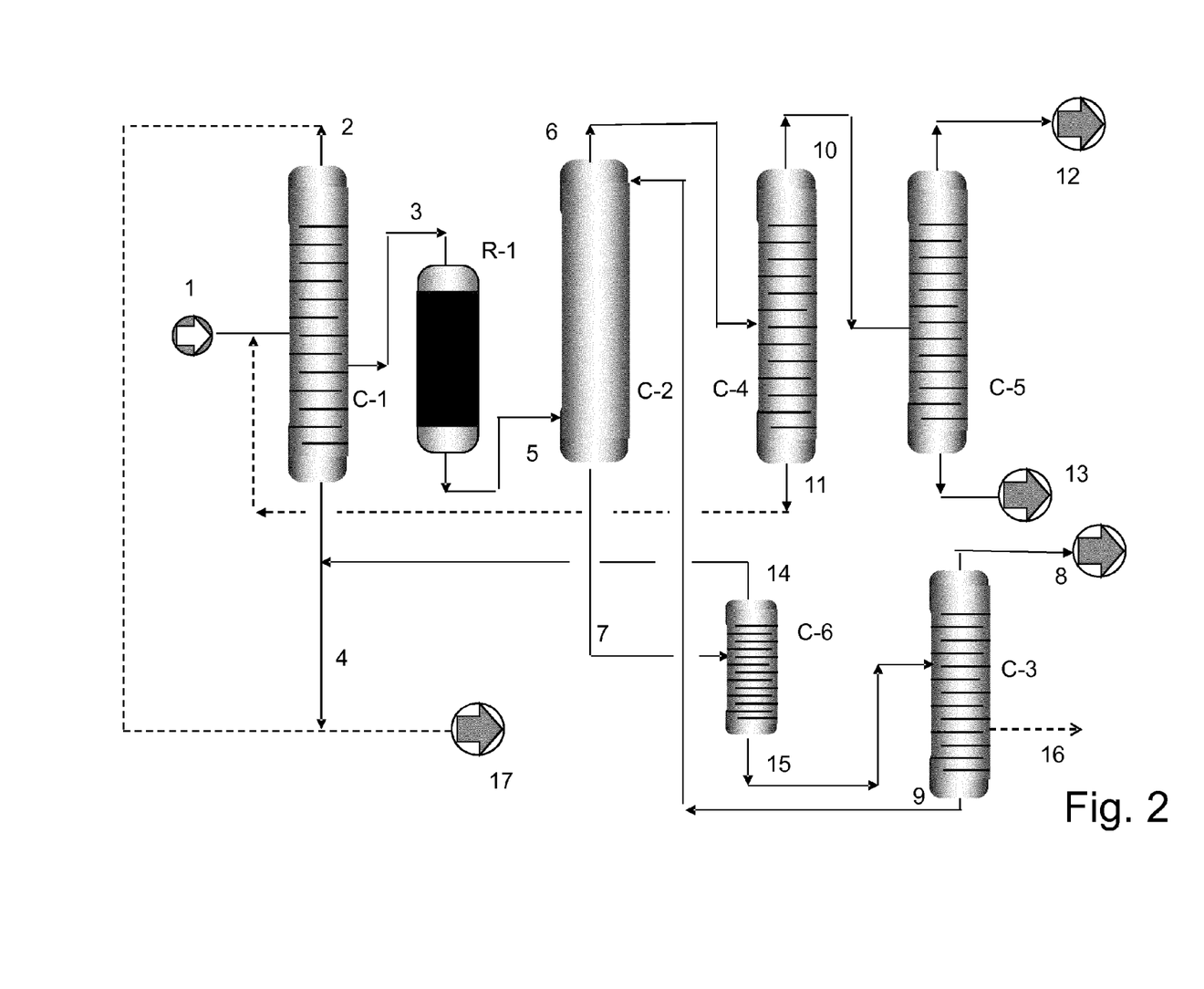
FIG. 2: Scheme for the production of high-purity isobutene substantially analogous to FIG. 1, except that the stream (7) containing methanol and water is fed to a fractionation column (C-6).

FIG. 2 shows a scheme for the production of high-purity isobutene substantially analogous to that of FIG. 1, except for stream (7) containing methanol and water which, before being fed to the fractionation column (C-3) for separation of the methanol from the water, is fed to a fractionation column (C-6), separating a stream (14) containing high-octane mixtures (HOM) essentially consisting of alcohols and ethers, at the head, and at the bottom a stream (15) of water and methanol fed to said fractionation column (C-3).

The stream (8) containing methanol (Grade A) obtained, is at a higher purity than that obtained in FIG. 1.

A stream (16) containing methanol, water and other oxygenated products in the cracking reaction can be possibly removed laterally from the fractionation column (C-3), which can be recycled to the cracking reactor (R-1) or joined with streams (2) and/or (4).

Figure 3:
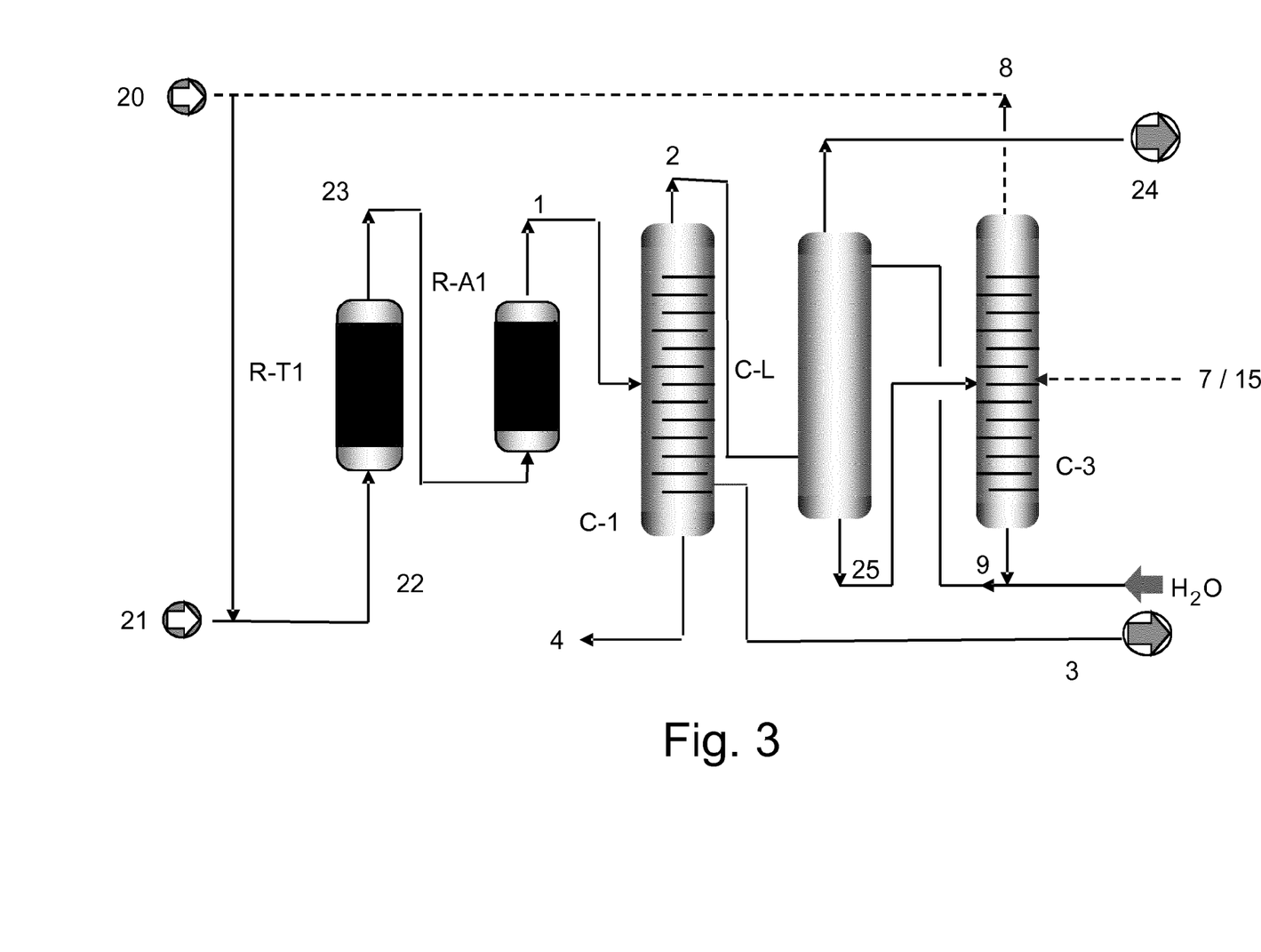
FIG. 3: Scheme of an integrated process for the production of MTBE and high-purity isobutene having one etherification area.

FIG. 3 shows a scheme of an integrated process for the production of MTBE and high-purity isobutene having one etherification area.

A stream (22) essentially consisting of methanol (20) and a $C_4$ cut (21), is sent to a first tubular etherification reactor (R-T1) and the outgoing product (23) to a second adiabatic etherification reactor (R-A1), obtaining a stream (1) prevalently containing MTBE, which is fed to the fractionation column (C-1), the same column (C-1) as the scheme of FIG. 1 or the scheme of FIG. 2.

The stream (3) removed laterally from said fractionation column (C-1), containing MTBE having a purity higher than 98% by weight, is sent to the cracking reactor (R-1) of the scheme of FIG. 1 or FIG. 2.

The stream (2) removed at the head from said fractionation column (C-1), containing $C_4$ hydrocarbons, among which non-converted isobutene and lighter compounds formed in the etherification reaction, is sent to a washing column (C-L) with water, separating, at the head, a stream (24) containing $C_4$ hydrocarbons from a stream (25) containing, at the bottom, methanol and water, which is sent to the fractionation column (C-3), the same column (C-3) as the scheme of FIG. 1, to which stream (7) is sent, or FIG. 2, to which stream (15) is sent, separating, at the head, a stream (8) containing methanol, which can be recycled to the etherification reactor and at the bottom, a stream containing water, recycled to the washing column (C-L) and to the column C-2 of FIGS. 1 and 2.

Figure 4:
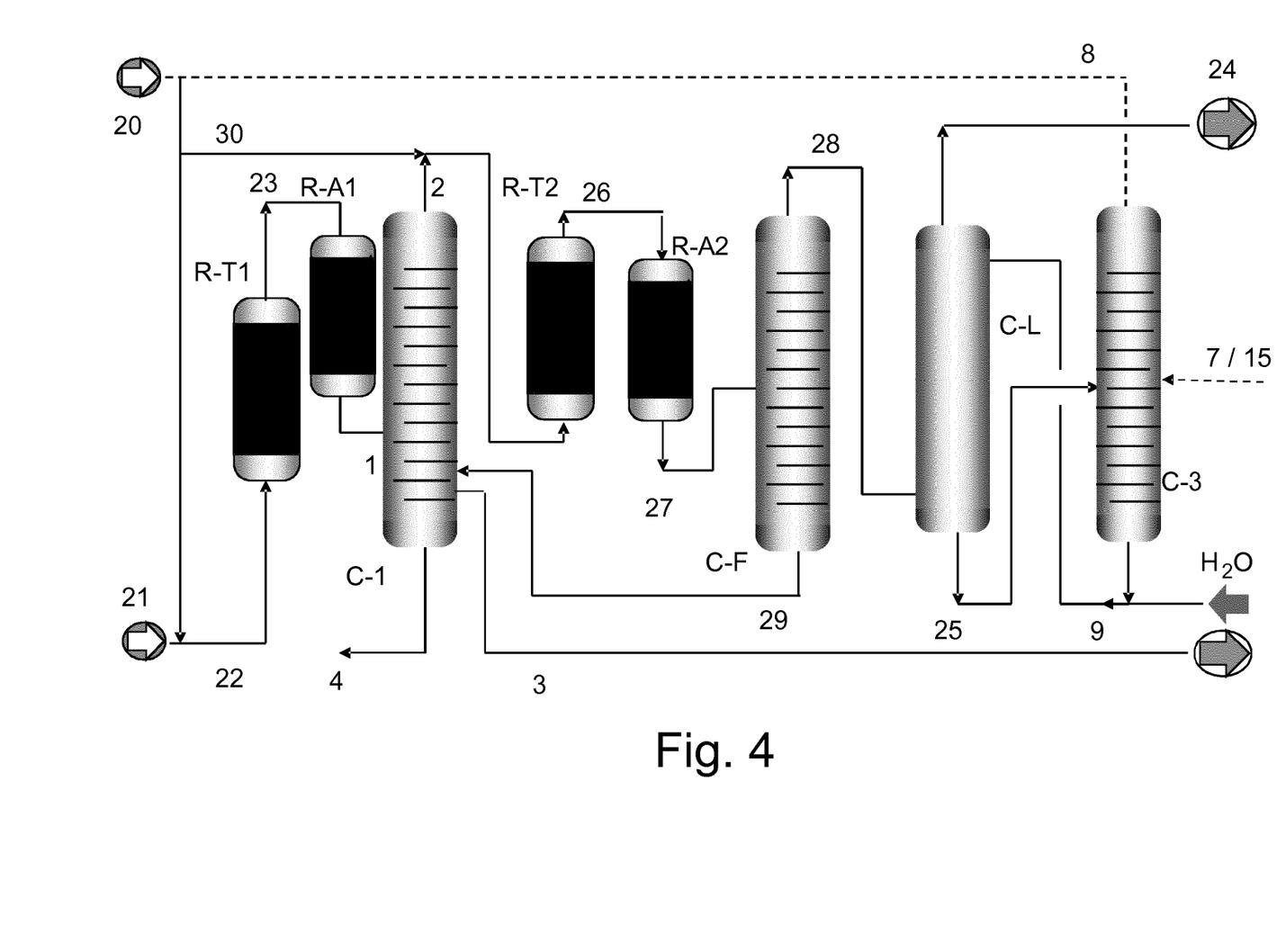
FIG. 4: Integrated process for the production of MTBE and high-purity isobutene, substantially analogous to FIG. 3, though having two etherification areas.

The stream (4), taken at the bottom from said fractionation column (C-1), containing MTBE and compounds heavier than MTBE, is removed from the plant to be sent to a gasoline pool. FIG. 4 shows an integrated process for the production of MTBE and high-purity isobutene, substantially analogous to that of FIG. 3, having, however, two etherification areas, so that the stream (2) removed at the head of the fractionation column (C-1), instead of being fed directly to the washing column (C-L), is sent, together with the methanol (30), to a second tubular etherification reactor (R-T2) and the outgoing product (26) to a second adiabatic etherification reactor (R-A2), obtaining a stream (27) prevalently containing MTBE, which is fed to a fractionation column (C-F), separating, at the head, a stream (28) containing $C_4$ hydrocarbons and methanol, which is sent to the washing column (C-L), and, at the bottom, a stream (29) prevalently containing MTBE, which is recycled to the fractionation column (C-1).

The invention claimed is:

1. A process for the production of high-purity isobutene which comprises feeding a stream containing MTBE (Methyl-Tert Butyl Ether) or ETBE (Ethyl-Tert Butyl Ether) into a fractionation area and obtaining a stream of high-purity MTBE or ETBE; and the following areas in sequence:
   a fractionation area for obtaining the stream of high-purity MTBE or ETBE;
   a cracking area of said stream of MTBE or ETBE for obtaining an outgoing stream containing isobutene and the relative alcohol, methanol or ethanol;
   a washing area with water of the stream leaving the cracking area for the recovery of the relative alcohol, in order to obtain a stream containing isobutene, the ether, and light compounds and a stream containing water and relative alcohol, with a relevant fractionation section for separating the washing water to be recycled to the same washing area from the relative alcohol;

a fractionation area of the stream containing isobutene, the ether, and light compounds for separating a stream of high-purity isobutene.

2. A process for the production of high-purity isobutene which comprises feeding a stream containing MTBE into a fractionation area and obtaining a stream of MTBE having a purity higher than 98% by weight; and the following areas in sequence:

a fractionation area for obtaining the stream of MTBE having a purity higher than 98% by weight;

a cracking area of said stream of MTBE for obtaining an outgoing stream containing methanol and isobutene;

a washing area with water of the stream leaving the cracking area for the recovery of the methanol to obtain a stream containing isobutene, MTBE, and light compounds and a stream containing water and methanol, with a relevant fractionation section for separating the washing water to be recycled to the same washing area from the methanol;

a fractionation area of the stream containing isobutene, MTBE, and light compounds for separating a stream of high-purity isobutene.

3. A process for the production of high-purity isobutene by means of MTBE cracking according to claim 2, comprising the following steps:

feeding a stream containing MTBE to one or more fractionation columns for the purification of the MTBE, separating a stream containing MTBE and lighter compounds of MTBE, a stream of MTBE having a purity higher than 98% by weight, and a stream containing MTBE and heavier compounds of MTBE;

feeding the stream of MTBE having a purity higher than 98% by weight to one or more cracking reactors obtaining an outgoing stream consisting of cracking products and non-converted reagents;

feeding said outgoing stream consisting of cracking products and non-converted reagents to a washing column with water, separating a stream containing isobutene, MTBE, and light compounds at the head, and a stream containing methanol and water at the bottom, in turn sent to one or more fractionation columns for separating the water, to be recycled to the washing column, from the methanol;

feeding the stream separated from the head of the washing column to a fractionation column for separating the isobutene from the MTBE, obtaining a stream containing isobutene and light compounds at the head, and a stream containing MTBE and heavier compounds at the bottom;

feeding the stream separated from the head of the fractionation column containing isobutene and light compounds to another fractionation column for the purification of the isobutene, obtaining a stream containing light compounds at the head and a stream of high-purity isobutene at the bottom.

4. The process according to claim 3, wherein the stream at the bottom of the washing column containing methanol and water is sent to a single fractionation column, separating a stream containing methanol at the head, and water recycled to the washing column at the bottom.

5. The process according to claim 3, wherein the stream at the bottom of the washing column containing methanol and water is sent to a first fractionation column, separating high-octane mixtures (HOM) containing alcohols and ethers at the head and a stream of water and methanol at the bottom, which is sent to a second fractionation column, separating a stream of high-purity methanol at the head, and the water recycled to the washing column at the bottom.

6. The process according to claim 3, wherein the stream containing MTBE at the bottom of the fractionation column for separating the isobutene from the MTBE is recycled to the fractionation column(s) for purifying the MTBE.

7. The process according to claim 5, wherein a stream, recycled to the cracking reactor(s), is also removed laterally from the second fractionation column of the stream of water and methanol.

8. An integrated process for the production of MTBE or ETBE and high-purity isobutene, starting from streams containing $C_4$ hydrocarbons, essentially comprising the following areas in sequence:

a fractionation area for obtaining a stream of high-purity MTBE or ETBE;

a cracking area of said stream of MTBE or ETBE for obtaining an outgoing stream containing isobutene and the relative alcohol, methanol or ethanol;

a washing area with water of the stream leaving the cracking area for the recovery of the relative alcohol, in order to obtain a stream containing isobutene, the ether, and light compounds, and a stream containing water and relative alcohol, with a relevant fractionation section for separating the washing water to be recycled to the same washing area from the relative alcohol;

a fractionation area of the stream containing isobutene, the ether, and light compounds, for separating a stream of high-purity isobutene, further integrated by the following areas:

an etherification area fed by streams containing $C_4$ hydrocarbons and the relative alcohol to obtain the stream containing the ether obtained, $C_4$ hydrocarbons, and the relative alcohol to be fed to the same fractionation area for obtaining the stream of high-purity MTBE or ETBE;

a possible additional etherification area with a relevant fractionation section, for separating a stream containing $C_4$ hydrocarbons and the relative alcohol and a stream containing the ether obtained, $C_4$hydrocarbons, and the relative alcohol to be fed to the first fractionation section;

a washing area with water of said stream containing $C_4$ hydrocarbons and the relative alcohol, coming from the fractionation area, to obtain the stream of high-purity ether, MTBE or ETBE, or from the fractionation section of the possible additional etherification area, with a relevant fractionation section, for separating the washing water to be recycled to the same washing area, said relevant fractionation section for separating the washing water being the same relevant fractionation section of the washing water of the stream leaving the cracking area for separating the stream containing isobutene.

9. The integrated process according to claim 8, for the production of MTBE and high-purity isobutene, starting from streams containing $C_4$ hydrocarbons, essentially comprising:

a fractionation area for obtaining a stream of MTBE having a purity higher than 98% by weight, a cracking area of said stream of MTBE for obtaining an outgoing stream containing methanol and isobutene, a washing area with water of the stream leaving the cracking area for the recovery of the methanol to obtain a stream containing isobutene, MTBE, and light compounds and a stream containing water and methanol, with a relevant fractionation section for separating the washing water to be recycled to the same washing area from the methanol, and a fractionation area of the stream containing isobutene, MTBE, and light compounds for separating a stream of high-purity isobutene;

integrated by the following areas:

an etherification area fed by streams containing $C_4$ hydrocarbons and methanol to obtain a stream containing MTBE, $C_4$ hydrocarbons, and methanol to be fed to the same fractionation area for obtaining the stream of MTBE having a purity higher than 98% by weight;

a possible additional etherification area with a relevant fractionation section, for separating a stream containing $C_4$ hydrocarbons and methanol and a stream containing MTBE, $C_4$ hydrocarbons and methanol to be fed to the first fractionation section;

a washing area with water of said stream containing $C_4$ hydrocarbons and methanol, coming from the fractionation area, to obtain the stream of MTBE having a purity higher than 98% by weight, or from the fractionation section of the possible additional etherification area, with a relevant fractionation section, for separating the washing water to be recycled to the same washing area, said relevant fractionation section for separating the washing water being the same relevant fractionation section of the washing area of the stream leaving the cracking area for separating the stream containing isobutene.

10. The integrated process according to claim 9, essentially comprising the steps of:

feeding a stream containing MTBE to one or more fractionation columns for the purification of the MTBE, separating a stream containing MTBE and lighter compounds of MTBE, a stream of MTBE having a purity higher than 98% by weight, and a stream containing MTBE and heavier compounds of MTBE;

feeding the stream of MTBE having a purity higher than 98% by weight to one or more cracking reactors obtaining an outgoing stream consisting of cracking products and non-converted reagents;

feeding said outgoing stream consisting of cracking products and non-converted reagents to a washing column with water, separating a stream containing isobutene, MTBE, and light compounds at the head, and a stream containing methanol and water at the bottom, in turn sent to one or more fractionation columns for separating the water, to be recycled to the washing column, from the methanol;

feeding the stream separated from the head of the washing column to a fractionation column for separating the isobutene from the MTBE, obtaining a stream containing isobutene and light compounds at the head, and a stream containing MTBE and heavier compounds at the bottom; and feeding the stream separated from the head of the fractionation column containing isobutene and light compounds to another fractionation column for the purification of the isobutene, obtaining a stream containing light compounds at the head and a stream of high-purity isobutene at the bottom;

integrated by the following steps:

feeding the stream containing $C_4$ hydrocarbons and methanol to one or more etherification reactors obtaining a stream containing MTBE, $C_4$ hydrocarbons, and methanol to be fed to the same fractionation column(s) for the purification of the MTBE;

feeding the stream containing MTBE and lighter compounds of MTBE, among which $C_4$ hydrocarbons, separated in the same fractionation column(s) for the purification of MBTE, to an additional washing column with water, separating a stream of $C_4$ hydrocarbons at the head, and a stream containing methanol and water at the bottom, in turn sent to one or more fractionation columns for separating the water, to be recycled to the washing column, from the methanol, the fractionation column(s) for separating the water from the methanol being the same fractionation column(s) to which the stream at the bottom of the washing column of the stream leaving the cracking reactor, is sent.

11. The integrated process according to claim 9, essentially comprising the steps of:

feeding a stream containing MTBE to one or more fractionation columns for the purification of the MTBE, separating a stream containing MTBE and lighter compounds of MTBE, a stream of MTBE having a purity higher than 98% by weight and a stream containing MTBE and heavier compounds of MTBE;

feeding the stream of MTBE having a purity higher than 98% by weight to one or more cracking reactors obtaining an outgoing stream consisting of cracking products and non-converted reagents;

feeding said outgoing stream consisting of cracking products and non-converted reagents to a washing column with water, separating a stream containing isobutene, MTBE, and light compounds at the head, and a stream containing methanol and water at the bottom, in turn sent to one or more fractionation columns for separating the water, to be recycled to the washing column, from the methanol;

feeding the stream separated from the head of the washing column to a fractionation column for separating the isobutene from the MTBE, obtaining a stream containing isobutene and light compounds at the head, and a stream containing MTBE and heavier compounds at the bottom; and feeding the stream separated from the head of the fractionation column containing isobutene and light compounds to another fractionation column for the purification of the isobutene, obtaining a stream containing light compounds at the head and a stream of high-purity isobutene at the bottom;

integrated by the following steps:

feeding the stream containing $C_4$ hydrocarbons and methanol to one or more etherification reactors obtaining a stream containing MTBE, $C_4$ hydrocarbons, and methanol to be fed to the same fractionation column(s) for the purification of MTBE;

feeding the stream containing MTBE and lighter compounds of MTBE, among which C4 hydrocarbons, separated in the same fractionation column(s) for the purification of MBTE, to another etherification reactor(s) obtaining a further stream containing MTBE, $C_4$ hydrocarbons, and methanol;

feeding the further stream containing MTBE, $C_4$ hydrocarbons, and methanol to another fractional column obtaining a stream containing $C_4$ hydrocarbons and methanol at the head and a stream containing MTBE at the bottom, which is recycled to the fractionation column for the purification of the MTBE;

feeding the stream at the head containing $C_4$ hydrocarbons and methanol to a further washing column with water, separating a stream of $C_4$ hydrocarbons at the head, and a stream containing methanol and water at the bottom, in turn sent to one or more fractionation columns for separating the water, to be recycled to the washing column, from the methanol, the fractionation column(s) for separating the water from the methanol being the same fractionation column(s) to which the stream at the bottom of the washing column of the stream leaving the cracking reactor, is sent.

12. The process according to claim 10, wherein the purification of the MTBE is effected in a single fractionation column.

13. The process according to claim 3, wherein the fractionation column for the purification of the MTBE operates at a pressure ranging from 1 to 12 $bar_g$.

14. The process according to claim 3, wherein the cracking reactor(s) operate at a temperature ranging from 100 to 300° C., at a pressure ranging from 1 to 10 $bar_g$.

15. The process according to claim 3, wherein the washing column of the stream leaving the cracking reactor(s) operates at a temperature ranging from 20 to 100° C., at a pressure ranging from 2 to 15 $bar_g$.

16. The process according to claim 3, wherein the fractionation column for the separation of isobutene from the MTBE operates at a pressure ranging from 2 to 10 $bar_g$.

17. The process according to claim 3, wherein the fractionation column for the purification of isobutene operates at a pressure ranging from 2 to 15 $bar_g$.

18. The process according to claim 3, wherein the fractionation column(s) of the stream containing methanol and water coming from the bottom of the washing column, operate at pressures ranging from atmospheric pressure to 10 $bar_g$.

19. The process according to claim 10, wherein the etherification reactor(s) operate in liquid phase.

20. The process according to claim 19, wherein the etherification reactor(s) operate at temperatures ranging from 20 to 150° C., and at a pressure below 50 $bar_g$.

21. The process according to claim 10, wherein the further washing column of the stream containing $C_4$ hydrocarbons and methanol operates at a temperature ranging from 20 to 100° C., and at a pressure ranging from 2 to 30 $bar_g$.

* * * * *